(12) United States Patent
Chen et al.

US008871736B2

(10) Patent No.: US 8,871,736 B2
(45) Date of Patent: *Oct. 28, 2014

(54) MAINTENANCE OF PLATELET INHIBITION DURING ANTIPLATELET THERAPY

(75) Inventors: Lisa Ruderman Chen, Rye, NY (US);
Simona Skerjanec, Pittstown, NJ (US);
Dawn Bell, Morristown, NJ (US);
Steven Steinhubl, Lexington, KY (US)

(73) Assignee: The Medicines Company, Parsippany, NJ (US)

( * ) Notice: Subject to any disclaimer, the term of this patent is extended or adjusted under 35 U.S.C. 154(b) by 725 days.

This patent is subject to a terminal disclaimer.

(21) Appl. No.: 12/990,332

(22) PCT Filed: May 13, 2009

(86) PCT No.: PCT/US2009/043820
§ 371 (c)(1),
(2), (4) Date: Aug. 15, 2011

(87) PCT Pub. No.: WO2009/140407
PCT Pub. Date: Nov. 19, 2009

(65) Prior Publication Data
US 2011/0288043 A1    Nov. 24, 2011

Related U.S. Application Data

(60) Provisional application No. 61/127,424, filed on May 13, 2008.

(51) Int. Cl.
*A61K 31/70* (2006.01)
*A01N 43/04* (2006.01)
*A61K 31/535* (2006.01)
*A61K 31/4365* (2006.01)
*A61K 31/7076* (2006.01)
*A61K 31/00* (2006.01)

(52) U.S. Cl.
CPC ......... *A61K 31/4365* (2013.01); *A61K 31/7076* (2013.01); *A61K 31/00* (2013.01)
USPC .......................................... 514/47; 514/231.5

(58) Field of Classification Search
None
See application file for complete search history.

(56) References Cited

U.S. PATENT DOCUMENTS

| 4,529,596 | A | * | 7/1985 | Aubert et al. ............... 514/233.8 |
| 5,288,726 | A | * | 2/1994 | Koike et al. .................... 514/301 |
| 5,721,219 | A | | 2/1998 | Ingall |
| 5,955,447 | A | | 9/1999 | Ingall et al. |
| 6,114,313 | A | | 9/2000 | Bland |
| 6,130,208 | A | | 10/2000 | Broadhead |
| 6,693,115 | B2 | * | 2/2004 | Asai et al. ..................... 514/301 |
| 6,861,424 | B2 | | 3/2005 | Bryant |
| 8,680,052 | B1 | * | 3/2014 | Arculus-Meanwell et al. ............................ 514/14.7 |
| 2006/0121086 | A1 | | 6/2006 | Boyer |
| 2006/0270607 | A1 | | 11/2006 | Dixon |
| 2007/0082840 | A1 | | 4/2007 | Porter |
| 2007/0254324 | A1 | | 11/2007 | Rechner |
| 2011/0112030 | A1 | | 5/2011 | Arculus-Meanwell |
| 2012/0141468 | A1 | | 6/2012 | Chen et al. |
| 2013/0040898 | A1 | | 2/2013 | Johansson et al. |
| 2013/0190265 | A1 | | 7/2013 | Arculus-Meanwell et al. |
| 2013/0303477 | A1 | | 11/2013 | Chen et al. |
| 2013/0303478 | A1 | | 11/2013 | Chen et al. |
| 2013/0316968 | A1 | | 11/2013 | Chen et al. |
| 2013/0324492 | A1 | | 12/2013 | Chen et al. |

FOREIGN PATENT DOCUMENTS

| WO | WO-2005-097814 | 10/2005 |
| WO | WO-2006-119507 | 11/2006 |
| WO | 2007024472 | 3/2007 |
| WO | WO-2011-134478 | 11/2011 |
| WO | WO-2013-025476 | 2/2013 |

OTHER PUBLICATIONS (S) Beers et al. (eds.), "Coronary Artery Disease," Chapter 73 in The Merck Manual of Diagnosis and Therapy, 18th Edition, Merck & Co., Inc., Rahway, NJ, Jan., 2006, only title pages and text pp. 626-652 supplied.*
(R) Porter et al. (eds.), a portion of "Coronary Artery Disease," Chapter 210 in The Merck Manual of Diagnosis and Therapy, 19th Edition, Merck & Co., Inc., Rahway, NJ, 2011, only title pages and text pp. 2087-2110 supplied.*
(S) Beers et al. (eds.), "Coronary Artery Disease," Chapter 73 in The Merck Manual of Diagnosis and Therapy, 18th Edition, Merck & Co., Inc., Rahway, NJ, Jan. 2006, only title pages and text pp. 626-652 supplied.*
The Extended European Search Report issued on Apr. 11, 2012 in the related European Application No. 09747490.2.
Accumetric, LLC, "VerifyNow User System User Manual," 2009.
Bonello et al., "Consensus and Future Directions on the Definition of High On-Treatment Platelet Reactivity to Adenosine Diphosphate," J Am Coll Cardiol, 2010; 56:919-933.
Gurbel et al., "Oral Dosing of PRT060128, a Novel Direct-acting, Reversible P2Y12 Antagonist Overcomes High Platelet Reactivity in Patients Non-responsive to Clopidogrel Therapy," Circulation. 2008;118:S_972, abstract.

(Continued)

*Primary Examiner* — Lawrence E Crane
(74) *Attorney, Agent, or Firm* — Frommer Lawrence & Haug LLP

(57) ABSTRACT

A method of treating or preventing a disease or condition in a subject that was previously treated with at least one thienopyridine is described. The method includes administering to the subject an effective amount of at least one reversible, short-acting P2Yi2 inhibitor. The described method can be used for subjects diagnosed with symptoms such as stable or unstable angina, vascular ischemic events, atherosclerosis, acute coronary syndrome, as well as STEMi or N-STEMI. The described method can also be used for patients having previously received a stent, such as a bare metal stent or a drug-eluting stent, and the treatment or prevention of stent thrombosis. The method can be used prior to, during, or after an invasive procedure such as coronary artery bypass grafting, percutaneous coronary intervention, or other general surgical procedure.

30 Claims, 2 Drawing Sheets

(56) References Cited

OTHER PUBLICATIONS

Gurbel et al., "Peri-operative platelet function testing: the potential for reducing ischaemic and bleeding risks," Thromb Haemost. Aug. 2011;106(2):248-52.

Kunapauli et al., "ADP receptors—targets for developing antithrombotic agents," Curr Pharm Des. 2003;9(28):2303-16.

Lepanalo et al., "Antiplatelet effect of clopidogrel in patients with aspirin therapy undergoing percutaneous coronary interventions—limited inhibition of the P2Y12 receptor," Thromb Res. Jun. 2009;124(2):193-8.

Price et al., "Standard- vs high-dose clopidogrel based on platelet function testing after percutaneous coronary intervention: the GRAVITAS randomized trial," JAMA. Mar. 16, 2011;305(11):1097-105.

Storey et al., "Comparison of the pharmacodynamic effects of the platelet ADP receptor antagonists clopidogrel and AR-C69931MX in patients with ischaemic heart disease," Platelets. Nov. 2002;13(7):407-13.

Storey et al., "Inhibition of platelet aggregation by AZD6140, a reversible oral P2Y12 receptor antagonist, compared with clopidogrel in patients with acute coronary syndromes," J Am Coll Cardiol. Nov. 6, 2007;50(19):1852-6.

Voisin et al., "Are P2Y12 reaction unit (PRU) and % inhibition index equivalent for the expression of P2Y12 inhibition by the VerifyNow® assay? Role of haematocrit and haemoglobin levels," Thromb Haemost. Aug. 2011;106(2):227-9.

Brilakis et al., "Perioperative Management of Patients With Coronary Stents," J Am Coll Cardiol, 2007; 49:2145-2150.

The International Search Report and Written Opinion by the International Searching Authority, issued on Jun. 30, 2009, in the PCT application No. PCT/US09/43820.

The International Search Report and Written Opinion by the International Searching Authority, issued on Jun. 11, 2009, in the PCT application No. PCT/US09/42681.

Dovlatova et al., "Competition Between Reversible and Irreversible P2Y12 Antagonists and Its Influence on ADP-Mediated Platelet Activation, " Abstract, J Thromb Haemost 2007; 5 Supplement 2: P-S-340.

Greenbaum et al., "Initial experience with an intravenous P2Y12 platelet receptor antagonist in patients undergoing percutaneous coronary intervention: results from a 2-part, phase II, multicenter, randomized, placebo- and active-controlled trial," Am Heart J. 2006 Mar;151(3):689.e1-689.e10.

U.S. Appl. No. 13/904,778, filed May 29, 2013, Arculus-Meanwell et al.

Firstenberg, M.S., et al., P4-Safety and Efficacy of Cangrelor, An Intravenous, Short-Acting Platelet Inhibitor in Patients Requiring Cardiac Surgery, American Association for Thoracic Surgery, 2012.

Ahrens, I., et al., Novel antiplatelet therapies following percutaneous coronary interventions, Current Opinion in Investigational Drugs, 2009, pp. 902-911, vol. 10, No. 9.

Angiolillo, D.J., et al., Bridging antiplatelet therapy with cangrelor in patients undergoing cardiac surgery: a randomized controlled trial, Supplementary Online Content, JAMA, 2012, pp. 265-274, vol. 307, No. 3.

Angiolillo, D.J., et al., Bridging Antiplatelet Therapy With Cangrelor in Patients Undergoing Cardiac Surgery: A Randomized Controlled Trial, Original Contribution, JAMA, 2012, pp. 265-274, vol. 307, No. 3.

Angiolillo, D.J., et al., Pharmacodynamic effects of cangrelor and clopidogrel: the platelet function substudy from the cangrelor versus standard therapy to achieve optimal management of platelet inhibition (CHAMPION) trials, J.Thromb Thr., 2012, pp. 44-55, vol. 34.

Becker, R.C., et al., Management of Platelet-Directed Pharmacotherapy in Patients With Atherosclerotic Coronary Artery Disease Undergoing Elective Endoscopic Gastrointestinal Procedures, JACC, 2009, pp. 2261-2276, vol. 54, No. 24.

Desai, N. R., et al., The State of Periprocedural Antiplatelet Therapy After Recent Trials, JACC: Cardiovascular Interventions, 2010, pp. 571-583, vol. 3, No. 6.

Sabatine, M.S., Novel antiplatelet strategies in acute coronary syndromes, Cleve Clin J Med, 2009, pp. S8-S15, vol. 76, Supp. 1.

Siddique, A., et al., New antiplatelet drugs: beyond aspirin and clopidogrel, Int. J. Clin. Pract., 2009, pp. 776-789, vol. 63, No. 5.

Norgard, N. B., Cangrelor: a novel $P2Y_{12}$ receptor antagonist, Expert Opin. Investig. Drugs, 2009, pp. 1219-1230, vol. 18, No. 8.

Oestreich, J.H., et al., Cangrelor in percutaneous coronary intervention, Expert Rev. Clin. Pharmacol., 2009, pp. 137-145, vol. 2, No. 2.

Paikin, J.S., et al., New antithrombotic agents—insights from clinical trials, Nature Reviews-Cardiology, 2010, pp. 498-509, vol. 7.

Ferreiro, J.L., et al., Cangrelor: a review on its mechanism of action and clinical development, Expert Rev. Cardiovasc. Ther., 2009, pp. 1195-1201, vol. 7, No. 10.

Akers, W.S., et al., Pharmacokinetics and Pharmacodynamics of a Bolus and Infusion of Cangrelor: A Direct, Parenteral P2Y12 Receptor Antagonist, The J Clin. Pharmacol, 2009, pp. 26-35, vol. 50.

Angiolillo, D.J., et al., Clinical overview of promising nonthienopyridine antiplatelet agents, AHJ, 2008, pp. S23-S28, vol. 156, No. 2, Supp. 1.

Bassand, J-P, Unmet needs in antiplatelet therapy, EHJ Supplements, 2008, pp. D3-D11, vol. 10, Supp. D.

Dalal, A.R., et al., Brief review: Coronary drug-eluting stents and anesthesia, Can J Anesth, 2006, pp. 1230-1243, vol. 53, No. 12.

Diaz-Ricart, M., et al., Cangrelor Tetrasodium, Drugs of the Future, 2008, pp. 101-110, vol. 33, No. 2.

Fugate, S.E., et al., Cangrelor for Treatment of Coronary Thrombosis, The Annals of Pharmacotherapy, 2006, pp. 925-930, vol. 40.

Storey, R.F., et al., Comparison of the pharmacodynamic effects of the platelet ADP receptor antagonists clopidogrel and AR-C69931MX in patients with ischaemic heart disease, Platelets, 2002, pp. 407-413, vol. 13.

Greenbaum, A.B., et al., Preliminary experience with intravenous $P2Y_{12}$ platelet receptor inhibitions as an adjunct to reduced-dose alteplase during acute myocardial infarction: Results of the Safety, Tolerability and Effect on Patency in acute Myocardial Infarction (STEP-AMI) angiographic trial, 2007, pp. 702-709, vol. 154, No. 4.

Steinhubl, S., et al., Optimizing Platelet $P2Y_{12}$ Inhibition for Patients Undergoing PCI, Cardiovascular Drug Reviews, 2007, pp. 188-203, vol. 25, No. 2.

Krajewski, S., et al., Short-acting $P_2Y_{12}$ blockade to reduce platelet dysfunction and coagulopathy during experimental extracorporeal circulation and hypothermia, BJA, 2012, pp. 912-921, vol. 108, No. 6.

Testa, L., et al., Current Concepts on Antiplatelet Therapy: Focus on the Novel Thienopyridine and Non-Thienopyridine Agents, Advances in Hematology, 2010, pp. 1-7, vol. 2010, Article ID 595934.

Ueno, M., et al., Update on the clinical development of cangrelor, Expert Rev Cardiovasc Ther, 2010, pp. 1069-1077, vol. 8, No. 8.

Xiang, B., et al., The $P2Y_{12}$ Antagonists, 2MeSAMP and Cangrelor, Inhibit Platelet Activation through $P2Y_{12}/_i$-Dependent Mechanism, PLOS One, 2012, pp. 1-10, vol. 7, Issue 12.

Straub, A., et al., Evidence of Platelet Activation at Medically Used Hypothermia and Mechanistic Data Indicating ADP as a Key Mediator and Therapeutic Target, JAHA, 2011, pp. 1607-1016.

Oliphant, C.S., et al., Emerging $P2Y_{12}$ Receptor Antagonists: Role in Coronary Artery Disease, Current Vascular Pharmacology, 2010, pp. 93-101, vol. 8, No. 1.

Firstenberg, M.S., et al., Safety and Efficacy of Cangrelor, an Intravenous, Short-Acting Platelet Inhibitor in Patients Requiring Coronary Artery Bypass Surgery, The Heart Surgery Forum, 2013, pp. E60-E69, vol. 16, No. 2.

Bhatt, D.L., et al., Effect of Platelet Inhibition with Cangrelor during PCI on Ischemic Events, Original Article, N Engl J Med, 2013, pp. 1303-1313, vol. 368, No. 14.

Bhatt, D.L., et al., Effect of platelet inhibition with cagrelor during PCI on ischemic events, 2013, N Engl J Med, pp. 1-15. Supplementary Appendix, Champion Phoenix.

(56) References Cited

OTHER PUBLICATIONS

International Search Report and Written Opinion by the International Searching Authority, issued on Jan. 3, 2014, in the PCT Application No. PCT/US2013/048735.
Angiolillo DJ, et al., Randomized Comparison of a High Clopidogrel Maintenance Dose in Patients with Diabetes Mellitus and Coronary Artery Disease, Circulation, 2007, 708-716, 115.
Examination Report issued on Aug. 21, 2013 in the related European Application No. 09747490.2.
Office Action issued on Jun. 4, 2013 in the related Chinese Application No. 200980126678.1.
Office Action issued on Jun. 11, 2013 in the related Japanese Application No. 2011-509659.

* cited by examiner

MAINTENANCE OF PLATELET INHIBITION DURING ANTIPLATELET THERAPY

CROSS-REFERENCES TO RELATED APPLICATIONS

This application is a National Stage Entry under 35 U.S.C. §371 of PCT/US09/043,820 filed on May 13, 2009, which claims priority to U.S. provisional application Ser. No. 61/127,424 filed on May 13, 2008. Each of the above-referenced applications is incorporated herein by reference.

FIELD OF THE INVENTION

The instant invention relates to the field of platelet inhibition, and in particular to methods of inhibiting platelet aggregation and related activities in patients previously treated with thienopyridines.

BACKGROUND OF THE INVENTION

Anti-platelet therapy has been shown to reduce clinical ischemic events and improve outcomes for acute coronary syndrome (ACS) patients. Currently, the approved anti-platelet products include aspirin and thienopyridines, such as clopidogrel and ticlopidine. One of the most widely prescribed thienopyridines is clopidogrel, which is also known as Plavix®.

Physicians often prescribe a dual anti-platelet therapy, which include aspirin and a thienopyridine, such as clopidogrel, for patients who have been diagnosed with acute coronary syndromes (ACS) or for patients who are showing symptoms associated with ACS as a first line treatment. Pending further examinations, these patients may continue with this treatment or receive other treatments such as coronary artery bypass grafting (CABG) and PCI. Consistent with this practice, current ACC/AHA guidelines recommend immediate initiation of dual anti-platelet therapy of clopidogrel and aspirin after a patient is diagnosed with ACS. Similarly, patients that have received a bare metal stent or drug-eluting stent are also put on aspirin and Plavix® for an extended period of time to prevent an ischemic event.

For many patients, this dual anti-platelet therapy provides tremendous clinical benefits, and minimizes the risks of ischemic events, such as heart attack and stroke. However, for certain patients, this therapy does have problems. Side effects from the use of thienopyridines include severe neutropenia, thrombotic thrombocytopenic purpura and increased incidence of hemorrhage, including gastrointestinal hemorrhage and cerebral hemorrhage. Furthermore, it has been observed that patients receiving the dual anti-platelet therapy experience an increased need for blood transfusions and incidence of bleeding complications while undergoing surgery and other invasive procedures. This is particularly true for ACS patients who often receive surgery, such as CABG and PCI, and other invasive procedures, such as implantation of a bare metal stent (BMS) or drug-eluting stent (DES).

Due to these concerns, for many patients who undergo surgery or other invasive procedures as subsequent treatments, continuation of the dual anti-platelet therapy of aspirin and clopidogrel is not desirable. Current ACC/AHA and STS guidelines recommend cessation of clopidogrel and aspirin before any non-emergent cardiac surgical procedures in order to minimize risk of bleeding during surgery.

Further complicating the matter, aspirin and thienopyridines are both irreversible, long-acting platelet antagonists. Reversal of the inhibition of platelet function occurs only as new platelets are generated and therefore even after discontinuation of aspirin and thienopyridines, their effect lasts several days before being completely eliminated. Consequently, a patient is often required to stop the dual anti-platelet therapy and wait for five to seven days before any surgical or invasive procedure can be performed.

As a result, physicians often face the difficult choice of discontinuing clopidogrel and aspirin prior to surgery and risking a potential ischemic event in the unprotected perioperative period or delaying surgery until after the time at which clopidogrel is no longer required.

Therefore, a need exists for additional anti-platelet therapies where conventional treatments, such as thienopyridine treatment (including clopidogrel or Plavix®) cannot be used, for example, where the effectiveness of the treatment has decreased over time, where the treatment is contraindicated, or where the treatment cannot be administered to the subject (such as an orally administered therapy). Further, in view of the long-lasting and irreversible side effects of thienopyridine, a new therapy for patients who are undergoing surgery or other invasive procedures, and who have discontinued prior treatment of aspirin and thienopyridines, is needed. Such therapies would allow suppression of platelet activities prior to, during, and/or after an invasive procedure without an increased risk of excessive or irreversible bleeding. This new therapy would also maintain platelet inhibition at acceptable levels and allow for rapid restoration of platelet function after discontinuation so that patients may undergo invasive procedures without increasing the risk of bleeding complications.

SUMMARY OF THE INVENTION

The present application is directed to methods for inhibiting platelet activities, such as aggregation, in subjects in which conventional thienopyridine therapy cannot be used or is no longer effective. As an example, the present application describes a method of treating or preventing an ischemic event in a subject in need thereof, who has been previously treated with a thienopyridine, aspirin or both.

In particular, the present application describes a method of treating or preventing an ischemic event in a subject, comprising administering an effective amount of at least one reversible, short-acting $P2Y_{12}$ inhibitor to a subject in need of such treatment, wherein the subject has undergone previous treatment with at least one thienopyridine, aspirin or both. In a preferred embodiment, the method is performed in a subject before, during, and/or after an invasive procedure, such as a surgical procedure. The present application further describes a method of inhibiting platelet activities, such as platelet aggregation, by administering to the subject in need thereof an effective amount of at least one reversible, short-acting $P2Y_{12}$ inhibitor upon discontinuation of aspirin or at least one thienopyridine, or both.

Examples of reversible, short-acting $P2Y_{12}$ inhibitors include, without limitations, cangrelor, ticagrelor and PRT060128. Additional compounds may also be obtained using the methods described in U.S. Pat. No. 5,721,219, or the methods well-known to a person skilled in the art. Examples of thienopyridines include, without limitations, clopidogrel, ticlopidine, prasugrel, and such other compounds having similar properties.

In methods of treatment where a scheduled cessation of anti-platelet treatment is desirable, such as during an invasive procedure, administration of a reversible, short-acting $P2Y_{12}$ inhibitor can begin several days prior to the invasive procedure, and end several hours prior to the procedure. One specific example is to administer a reversible, short-acting $P2Y_{12}$ inhibitor beginning 7 days prior to an invasive procedure and ending 1 hour prior to the procedure. It should be noted that the methods or the duration of administering a reversible, short-acting $P2Y_{12}$ inhibitor often vary depending on which reversible, short-acting $P2Y_{12}$ inhibitor is used.

The described methods can be used for subjects diagnosed with symptoms such as stable or unstable angina, vascular ischemic events, atherosclerosis, acute coronary syndrome, including STEMI or N-STEMI. The described methods can also be used for patients having previously received a stent, such as a bare metal stent or a drug-eluting stent, and the treatment or prevention of stent thrombosis.

The described methods can be used for a subject before, during, and/or after an invasive procedure, such as coronary artery bypass grafting, orthopedic surgeries, urological surgeries, percutaneous coronary intervention, other general invasive procedures, such as endarterectomy, renal dialysis, cardio-pulmonary bypass, endoscopic procedures or any medical, surgical, or dental procedure that could potentially lead to excessive bleeding or hemorrhage.

Further, the described methods of the present invention can be used in a subject who cannot be orally administered platelet inhibiting therapies and, for whatever reason, cannot be administered long lasting thienopyridines, such as clopidogrel or Plavix®

BRIEF DESCRIPTION OF THE FIGURES

Understanding of the present invention will be facilitated by consideration of the following detailed description of the embodiments of the present invention taken in conjunction with the accompanying drawings, in which like numerals refer to like parts and in which.

DETAILED DESCRIPTION OF THE PREFERRED EMBODIMENTS

Figure 1:
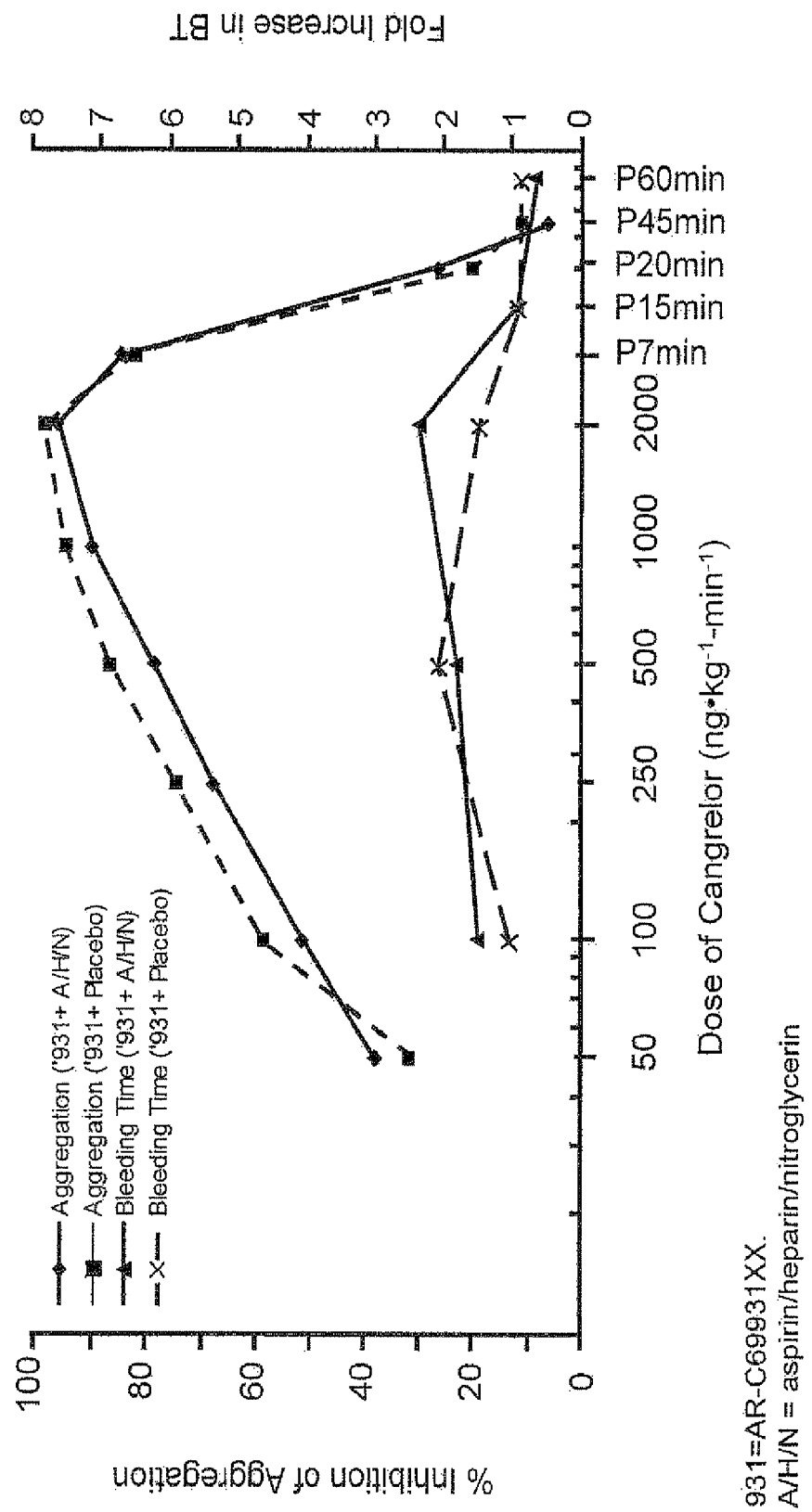
FIG. 1 is a graphical presentation of the percent inhibition of ADP-induced platelet aggregation and effect on bleeding time.

It is to be understood that the figures and descriptions of the present invention have been simplified to illustrate elements that are relevant for a clear understanding of the present invention, while eliminating, for the purpose of clarity, many other elements found in typical antiplatelet therapies. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The present invention provides a method for at least partially inhibiting platelet activities for subjects having previously been administered a thienopyridine by discontinuing the thienopyridine and administering a reversible, short-acting platelet inhibitor for maintaining platelet inhibition. Such methods may be used prior to, during, and/or after an invasive procedure. Examples of platelet activities include platelet aggregation. Examples of such invasive procedures include coronary artery bypass grafting, orthopedic surgeries, urological surgeries, percutaneous coronary intervention, other general invasive procedures, such as endarterectomy, renal dialysis, cardio-pulmonary bypass, endoscopic procedures or any medical, surgical, or dental procedure that could result in excessive bleeding or hemorrhage to the patient. Platelet inhibition can be maintained at acceptable and targeted levels, and allows for rapid restoration of platelet function after discontinuation so that patients may undergo invasive procedures without increasing the risk of bleeding complications.

The described methods can be used for treating or preventing a disease or condition. For example, the described methods can be used for subjects diagnosed with symptoms of stable or unstable angina, vascular ischemic events, atherosclerosis, acute coronary syndrome, as well as STEMI or N-STEMI. The described methods can also be used for subjects having previously received a stent, such as a bare metal stent or a drug-eluting stent, for the treatment or prevention of stent thrombosis. While the present invention is generally targeted for use with human subjects, the described methods can be used on any living animal.

The present invention further provides a method for maintaining adequate $P2Y_{12}$ inhibition, with rapid reversibility, upon discontinuation of thienopyridines. For example, patients with indwelling drug-eluting stents are typically maintained on aspirin and clopidogrel to prevent stent thrombosis. Should these patients require a surgical procedure, cessation of clopidogrel increases the risk for ischemic events or stent thrombosis. Further, maintaining irreversible platelet inhibition with aspirin and a thienopyridine leads to unacceptable operative bleeding risk. As mentioned previously, cessation of clopidogrel may increase the incidence of ischemic events in the short-term due to a "rebound" effect of platelet activation (Ho et al JAMA 299(5):532-9 (2008); erratum JAMA 299(20):2390 (2208)). By providing effective platelet inhibition with a reversible, short-acting platelet inhibitor during the period of clopidogrel withdrawal, patients can be protected from ischemic events and also preserve normal hemostasis at the time of surgery.

As explained previously, dual antiplatelet therapy with clopidogrel and aspirin may reduce clinical ischemic events and may further improve outcomes for patients with ACS. For ACS patients undergoing surgical revascularization, $P2Y_{12}$ inhibition with clopidogrel before CABG significantly prevents ischemic events in surgical patients.

Reversible, short-acting $P2Y_{12}$ inhibitors have several advantages over their thienopyridine counterparts. For example, the thienopyridines, such as clopidogrel, ticloridine, and prasugrel, are pro-drugs that require metabolism for conversion to the active metabolite. In contrast to this, reversible, short-acting $P2Y_{12}$ inhibitors can directly act on the $P2Y_{12}$ receptor without any metabolic conversion. They often have relatively short half lives as compared to the thienopyridines. For example, the plasma half life of cangrelor is approximately less than 10 minutes, and allowing for a return to normal platelet function in a short period upon discontinuation. By reducing the need for a compound to be metabolized for activity, and by having a relatively short half life, reversible, short-acting $P2Y_{12}$ inhibitors are considered "reversible", meaning that full platelet functionality may return rather quickly as compared to thienopyridines.

As discussed herein, there are a number of circumstances under which thienopyridine therapy cannot be utilized to control platelet activity in a subject. For example, patients in acute setting are mostly sedated, on multiple IV agents, with impaired gastrointestinal absorption and often intubated. Under such circumstances, oral therapy (the primary means of thienopyridine administration) is not feasible and may be potentially hazardous as the patients cannot swallow oral agents.

In addition, acute disease management requires flexible treatments as the patient situation and risk changes frequently. An intravenous platelet inhibitor that achieves immediate effect without a requirement for absorption and metabolism to achieve rapid onset of effect (as opposed to oral therapy which requires absorption and potentially liver metabolism to convert inactive pro-drug to the active compound) with a short duration of action and reversible effect is critically important in the management of acutely ill patients.

As used herein, the term "reversible, short-acting $P2Y_{12}$ inhibitor" refers to a compound which inhibits $P2Y_{12}$ receptor activities, which has a fast onset time and a relatively short metabolism rate as compared to those of thienopyridines. Examples of a fast-acting, reversible $P2Y_{12}$ inhibitor include, without limitations, cangrelor, ticagrelor and PRT060128. It should be noted that the present invention is not limited to these examples. Additional compounds that have similar properties may also be used in the present invention.

One particularly preferred example of a reversible, short-acting $P2Y_{12}$ inhibitor is cangrelor. Cangrelor is a potent, direct, and reversible antagonist of the platelet $P2Y_{12}$ receptor. The binding of cangrelor to the $P2Y_{12}$ receptor inhibits platelet activation as well as aggregation when mediated in whole or in part via this receptor. Cangrelor can be derived completely from synthetic materials, and is an analogue of adenosine triphosphate (ATP), the natural antagonist for the $P2Y_{12}$ receptor. Cangrelor shows an immediate onset of effect (t½~5-6 min) and it can be administered as a bolus and/or infusion. It does not require GI absorption or liver metabolism to achieve therapeutic plasma concentrations required for its activity. Because Cangrelor's effect on platelets is reversible, it therefore enables homeostasis within a short period after discontinuation of infusion. As such, it is ideally positioned for use in acute situations where treatment flexibility is required, such as emergency room procedures, use in the ICU and peri-procedural setting and pre- and post-surgery recovery periods when platelet inhibition is an important component of patient management. A description of cangrelor and its related compounds can be found in U.S. Pat. No. 5,721,219 (Ingall et al.), the entire disclosure of which is incorporated by reference herein as if set forth in its entirety.

Yet another aspect of the present invention is a method of administering a reversible, short-acting $P2Y_{12}$ inhibitor upon discontinuation of a thienopyridine, aspirin or both for the purpose of maintaining platelet inhibition at least equivalent to the mean anticipated level of inhibition achieved by the thienopyridine, aspirin, or both. As noted above, the administering of the inhibitor can occur before, during, and/or after an invasive procedure in a subject.

As used herein, reference to platelet functions or activities includes all functions and activities that result from activation of the platelet $P2Y_{12}$ receptor, including platelet aggregation.

Reversible, short-acting $P2Y_{12}$ inhibitors, such as cangrelor, ticagrelor or PRT060128, can be administered using any of the various methods and delivery systems known to those skilled in the art. The administering can be performed, for example, intravenously, orally, via implant, transmucosally, transdermally, intramuscularly, intrathecally, and subcutaneously. According to one preferred embodiment, a reversible, short-acting $P2Y_{12}$ inhibitor may be administered intravenously or orally. It is contemplated that the reversible, short-acting $P2Y_{12}$ inhibitor can be administered intravenously in accordance with the present invention during an invasive procedure, such as surgery, when the patient is comatose, or any other such scenario where use of the oral administration of a platelet inhibitor is prohibited.

In the case of administering and ceasing the therapy prior to surgery in accordance with one embodiment of the present invention, such use allows patients to undergo surgery or other invasive procedures without excessive perioperative bleeding. For example, as described herein, cangrelor infusion can maintain platelet inhibition levels of approximately greater than or equal to 60% after discontinuation of clopidogrel and before the procedure begins.

To determine how to administer a reversible, short-acting $P2Y_{12}$ inhibitor or the amount of a reversible, short-acting $P2Y_{12}$ inhibitor to be administered, the pharmacokinetic profile of the reversible, short-acting $P2Y_{12}$ inhibitor can be analyzed using the methods well-known to a person skilled in the art.

For example, the pharmacokinetics of cangrelor has been shown to be substantially linear, and its steady-state plasma concentrations can be achieved in less than approximately 5 minutes following the administration of an intravenous infusion.

A dose-response relationship of cangrelor has been evaluated for inhibition of ADP induced platelet aggregation ex vivo. A dose-related inhibition was observed ranging from 10 ng/kg/min to 4000 ng/kg/min infusion. The dose-response curve for percentage inhibition of ADP induced platelet aggregation ex vivo was similar in male and female healthy volunteers, patients with unstable angina and in presence of other adjunctive therapy of aspirin, heparin and nitroglycerin. Cangrelor produced potent inhibition of ADP-induced platelet aggregation ex vivo with IC50 7.72+/−1.95 ng/mL. As may be seen in FIG. 1, over 80% inhibition was achieved at doses of about 0.5 ug/kg/min and above. Inhibition was rapidly reversible and platelet aggregatory response restored close to baseline within one hour of stopping the infusion. An infusion dose of approximately about 0.5 ug/kg/min of cangrelor can also maintain adequate antiplatelet activity during infusion in the targeted patient.

It has been determined that consistent and complete platelet inhibition can be maintained throughout cangrelor infusion with full recovery of platelet function within approximately one hour of infusion cessation. Clopidogrel administration at the termination of cangrelor infusion may lead to the expected degree of platelet inhibition, which may be measured by P-selectin expression, electrical impedance and light transmittance aggregometry.

In each of the embodiments of the present invention, the amount of reversible, short-acting $P2Y_{12}$ inhibitor to be administered to a subject can be determined by the attending physician. In general, however, a dose of between about 0.1 to about 3.0 µg/kg/min may be administered to the subject. Specific doses of 0.25, 0.5, 0.75, 1.0, 1.25, 1.5, 1.75, 2.0, 2.25, 2.5, 2.75 and 3.0 µg/kg/min may be administered to the subject.

The total amount of reversible, short-acting $P2Y_{12}$ inhibitor that may be administered to a subject may be between about 0.01 and 1000 mg per 24 hour period, with exemplary totals of about 0.5, 0.75, 1.0, 1.25, 1.5, 1.75, 2.0, and 2.5 mg per 24 hour period.

The skilled artisan will understand that the exact amount of reversible, short-acting $P2Y_{12}$ inhibitor to be administered to a subject will vary depending on the degree of platelet activity inhibition that is sought. For example, the amount of reversible, short-acting $P2Y_{12}$ inhibitor to be administered to a subject during an invasive procedure that will result in bleeding may be much less than the amount that would be administered when such a procedure is not being performed. Specific doses of 0.025, 0.05, 0.075, 0.10, 0.125, 0.15, 0.175, 0.20, 0.225, 0.25, 0.275, and 0.30, 0.325, 0.35, 0.375, 0.40, 0.425, 0.45, 0.475, 0.50, 0.525, 0.55, 0.575, 0.60, 0.625, 0.65, 0.675, 0.70, 0.725, 0.75, 0.775, 0.80, 0.825, 0.85, 0.875, 0.90, 0.925, 0.95, 0.975, and 1.0 µg/kg/min may be administered to the subject during an invasive procedure.

The reversible, short-acting $P2Y_{12}$ inhibitor may be administered as a continuous intravenous infusion or it may be administered in discrete doses, such as between 1 and 48 doses, or more, per 24 hour period.

The dosage of the reversible, short-acting $P2Y_{12}$ inhibitor may vary over time, with a lower dosage being initially administered, following by a increased dosage for a sustain period of time, with an optional decrease in the dosage prior to complete cessation of administration of the reversible, short-acting $P2Y_{12}$ inhibitor. Such a dosing regime may be used in conjunction with the concurrent cessation of thienopyridine and/or aspirin treatment and beginning of reversible, short-acting $P2Y_{12}$ inhibitor. Such a dosing regime can ensure a constant level of platelet activity inhibition.

The reversible, short-acting $P2Y_{12}$ inhibitor may be administered to a subject in a pharmaceutically acceptable formulation, comprising a reversible, short-acting $P2Y_{12}$ inhibitor and one or more pharmaceutically acceptable carriers or diluents. Such carriers and diluents are readily known to those of skill in the art.

Figure 2:
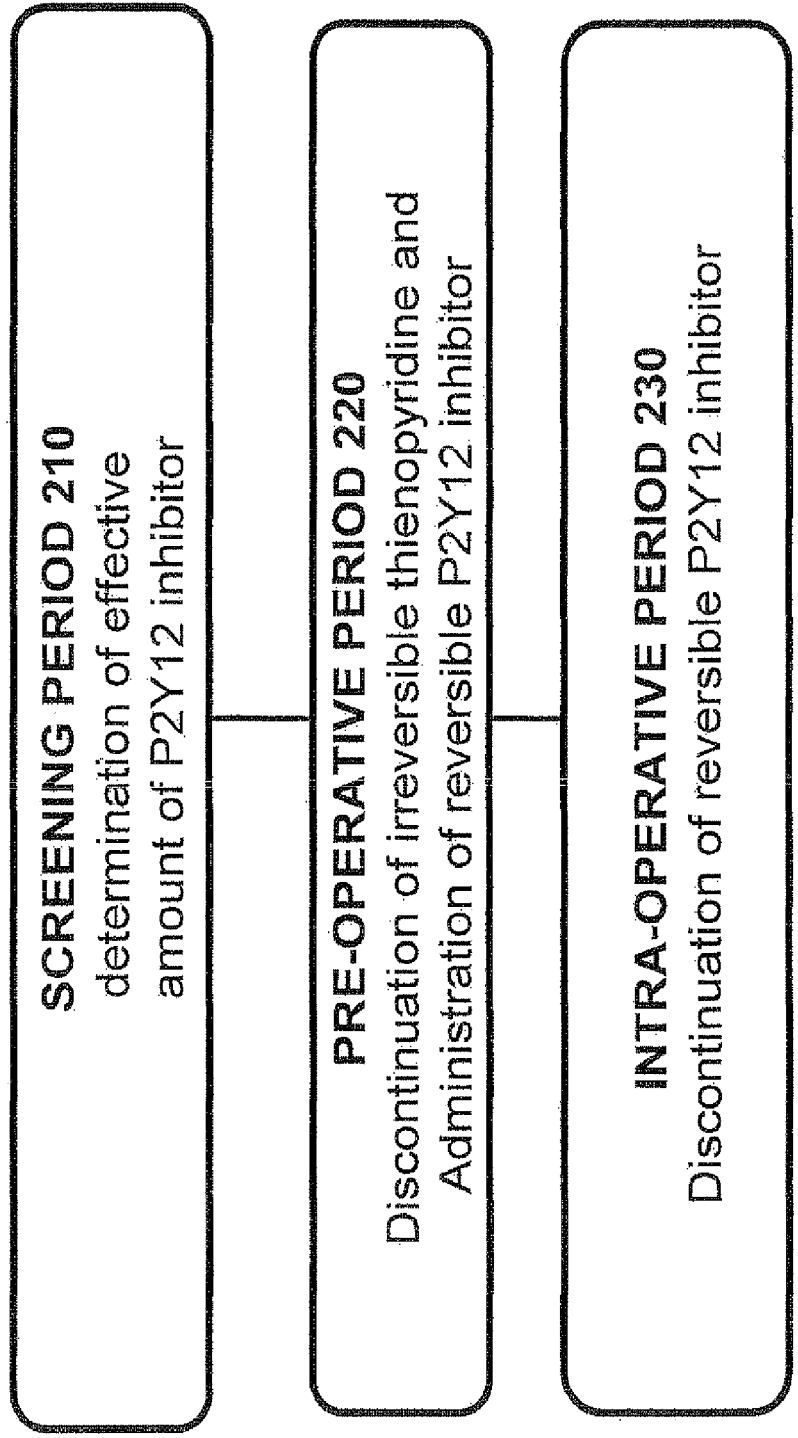
FIG. 2 is a flow chart of the time periods through which the present invention is performed.

Without limitations, FIG. 2 provides a brief summary as to how the methods described in the present invention may be used in a subject in need thereof. It should be understood that the method of the present invention is not limited to the procedure described in FIG. 2.

As shown in FIG. 2, a screening period 210 can be used for determining the dosage necessary for achieving inhibition of platelet aggregation of greater than a pre-determined level, for example, a level of approximately 60% platelet aggregation inhibition. A pre-operative period 220 of up to approximately 5 days prior to surgery can be used for administration of a reversible, short-acting $P2Y_{12}$ inhibitor. An intra-operative period 230 lasting from the discontinuation of the reversible, short-acting $P2Y_{12}$ inhibitor to the end of surgery can be used as needed During screening period 210, the dosage of a reversible, short-acting $P2Y_{12}$ inhibitor, necessary to achieve inhibition of platelet aggregation of greater than a pre-determined level, for example approximately 60%, can be determined. For example, intravenous infusion of a reversible, short-acting $P2Y_{12}$ inhibitor can be administered to a patient in doses typically ranging from 0.1 to 3.0 µg/kg/min, and particularly at doses of 0.5 µg/kg/min, 0.75 µg/kg/min, 1.0 µg/kg/min, 1.5 µg/kg/min and 2.0 µg/kg/min, until measured platelet inhibition is greater than the pre-determined level. Smaller or larger doses may also be used as needed to achieve the required level of platelet inhibition. In other forms, a reversible, short-acting $P2Y_{12}$ inhibitor can be administered at a daily dose of from 0.1 mg to 1000 mg, which may be in divided doses e.g. up to 6 times per day. The dosage of a reversible, short-acting $P2Y_{12}$ inhibitor for any particular patient can also be determined ahead of time, so as to reduce the need to give multiple doses to achieve the required level of platelet inhibition. In all instances where measurement of platelet inhibition is needed, a baseline value should be obtained to accurately determine when acceptable levels have been reached.

During pre-operative period 220, administration of a reversible, short-acting $P2Y_{12}$ inhibitor can be initiated the day the decision is made to discontinue clopidogrel or other thienopyridines and may be continued throughout pre-operative period 220. For example, patients can receive from at least approximately 48 hours of infusion of a reversible, short-acting $P2Y_{12}$ inhibitor and up to as much as approximately seven days of infusion. In one exemplary embodiment, a patient can undergo CABG after completion of a 5-day waiting period from the discontinuation of clopidogrel. In other embodiments, administration of a reversible, short-acting $P2Y_{12}$ inhibitor may be discontinued within a range from approximately one hour before surgery to approximately 3 hours before an invasive procedure, such as surgery. The dose of such a reversible, short-acting $P2Y_{12}$ inhibitor can remain constant or can be periodic during the treatment period. Treatment may then be terminated one hour before induction of anesthesia for the scheduled surgery.

Also during pre-operative period 220, any number of procedures and/or tests can be performed in conjunction with the present invention, such as hemoglobin, hematocrit, white blood cells, and platelet count testing; serum creatinine testing; measurement of inhibition of platelet activation; and assessment of concomitant medications, adverse events, serious adverse events and other various clinical endpoints. Additionally, procedures such as CK and CK-MB and VerifyNow $P2Y_{12}$ assays, for example, can be performed within 24 hours prior to surgery.

During intra-operative period 230, administration of a reversible, short-acting $P2Y_{12}$ inhibitor can be stopped between at least 1 hour and up to approximately 3 hours prior to administration of anesthesia for surgery. Basic standard of care treatment is used for the surgical period as understood by those having skill in the art. Collection of concomitant medications and assessments of adverse events, serious adverse events and clinical endpoints can also be performed during this period as needed.

Assessment of platelet function can be determined by use of the Accumetrics VerifyNow™ $P2Y_{12}$ (Accumetrics, San Diego, Calif.) assay. The VerifyNow™ $P2Y_{12}$ assay is a point of care device for the assessment of the level of inhibition of platelet activation specifically designed for patients exposed to thienopyridines. It should be understood that any assay system for determining levels of inhibition of platelet activation can be used, as understood by those having skill in the art. Blood samples for the VerifyNow™ $P2Y_{12}$ assay can be collected into Greiner Bio-One Vacuette partial fill blood collection tubes (2 mL fill volume) containing 3.2% citrate, or by other suitable means.

The VerifyNow™ $P2Y_{12}$ assay is a rapid platelet-function cartridge-based assay that activates platelets using adenosine diphosphate (ADP), but also uses prostaglandin E1 to suppress the ADP-induced P2Y1-mediated increase in intracellular calcium levels to increase the specificity of the test for inhibition of the $P2Y_{12}$ receptor. The test cartridge contains a lyophilized preparation of human fibrinogen coated beads, platelet agonist, buffer and preservative. Fibrinogen-coated microparticles are used to bind to available platelet receptors. When the activated platelets are exposed to the fibrinogen-coated microparticles, agglutination occurs in proportion to the number of available platelet receptors. The whole-blood citrate mixture is added to the cartridge, and agglutination between platelets and coated beads is recorded. The VerifyNow™ $P2Y_{12}$ device is a turbidimetric optical detection system, which measures platelet induced aggregation as an increase in light transmittance. Assay results are expressed in $P2Y_{12}$ reaction units (PRU) [Malinin et al, 2006]. VerifyNow™ $P2Y_{12}$ testing can be used at any time point as described herein to assess the level of inhibition of platelet activation.

According to another aspect of the present invention, additional medications can be allowed as concomitant medications. By way of non-limiting example, compounds such as aspirin, epsilon amino-caproic acid, tranexamic acid, and heparin can be used as concomitant medications.

EXAMPLES

Example 1

In a first example, cangrelor can be administered by intravenous infusion, and can be administered to patient groups in a step-wise fashion at pre-determined doses (0.5 μg/kg/min, 0.75 μg/kg/min, 1.0 μg/kg/min and 1.5 μg/kg/min) until platelet inhibition as measured by VerifyNow™ $P2Y_{12}$ reaches a level of greater than about 60% or until a dose of 2.0 μg/kg/min is reached.

The first set of patients can receive an infusion of about 0.5 μg/kg/min. If platelet inhibition as measured by VerifyNow™ $P2Y_{12}$ is determined to be less than about 60%, the second set of 5 patients can be administered about a 0.75 μg/kg/min intravenous infusion of cangrelor. If platelet inhibition as measured by VerifyNow™ $P2Y_{12}$ is determined to be less than about 60%, the third set of 5 patients can be administered about a 1.0 μg/kg/minute intravenous infusion of cangrelor. If platelet inhibition as measured by VerifyNow™ $P2Y_{12}$ is determined to be less than about 60%, the remaining groups can be administered about a 2.0 μg/kg/min intravenous infusion of cangrelor. Following the determination of the effective dosage of cangrelor to achieve platelet inhibition of greater than about 60% as measured by VerifyNow™ $P2Y_{12}$, a single infusion dose of cangrelor can be administered.

Patients can then be randomized into two arms to receive cangrelor versus standard of care. In the first arm, patients can receive only standard of care, in which clopidogrel can be discontinued after the need for surgery has been determined and a placebo infusion administered. In the second arm, a cangrelor infusion of the previously determined effective amount to achieve platelet inhibition of greater than about 60% as measured by VerifyNow™ $P2Y_{12}$ can be started in addition to standard of care when clopidogrel has been discontinued after the need for surgery has been determined. The infusions (cangrelor or matching placebo) can continue throughout the perioperative period. Patients can wait about 5 days after discontinuation of clopidogrel before undergoing surgery, in accordance with ACC/AHA and STS guidelines. Intravenous infusion of cangrelor can be discontinued between approximately 1 and 3 hours prior to surgery.

Example 2

In another example and in accordance with one embodiment of the present invention, the administration of the at least one reversible, short-acting P2Y12 inhibitor occurs during an invasive procedure being performed on the subject. In this manner, it is contemplated that the administration of the inhibitor would occur intravenously as the subject cannot take the therapy orally.

Example 3a

In another example and in accordance with another embodiment of the present invention, the administration of the at least one reversible, short-acting P2Y12 inhibitor occurs after an invasive procedure has been performed on the subject. The administration of the inhibitor in the post surgery scenario can occur in a variety of methods as described above.

It is contemplated that the administration of the inhibitor may also occur intravenously post surgery if the subject cannot take the therapy orally, for example, if the subject is comatose.

Example 3b

The Study for Using Cangrelor in Early Post-Operative Period

Current standard of care for anti-platelet maintenance therapy after PCI in patients with implanted stents is based on recommendations of the American College of Cardiology/American Heart Association (ACC/AHA) guidelines (Fleisher L A, et al., ACC/AHA 2007 guidelines on perioperative cardiovascular evaluation and care for noncardiac surgery: a report of the ACC/AHA Task Force on Practice Guidelines. Circulation. 2007 Oct. 23; 116(17):e418-99) that suggest an early initiation of dual anti-platelet therapy and continuation of maintenance therapy with aspirin and clopidogrel after PCI from 6 to 12 months, depending on the stent type, in order to prevent post-procedural stent thrombosis. Both aspirin and clopidogrel are irreversible platelet antagonists, therefore ACC/AHA guidelines recommend cessation of clopidogrel before non-emergent surgical procedures in order to minimize bleeding risks.

However, should patients with implanted stents require a surgical procedure, early cessation of clopidogrel would increase the risk for ischemic events and stent thrombosis due to a "rebound" effect of platelet activation (Berger et al., Circulation. 2002 Oct. 22; 106(17):2284-7; Ho et al. JAMA. 2008 Feb. 6; 299(5):532-9). Conversely, maintaining irreversible platelet inhibition with aspirin and clopidogrel leads to unacceptable operative bleeding risk (Fox et al., Circulation. 2004; 110; 1202-1208; Shim et al., J Thorac Cardiovasc Surg. 2007 July; 134(1):59-64; Pickard et al., Pharmacotherapy. 2008 March; 28(3):376-92. Review).

Because of the risk of bleeding from the surgical sites, surgeons prefer to avoid using anticoagulant agents in early post-operative period especially with irreversible oral therapy that will not allow predicting the level of platelet inhibition and fast recovery of platelet function when surgical procedure could be associated with high risk of post-operative bleeding.

It is well known that surgical interventions trigger platelet activation and aggregation, hence increasing the risk of stent thrombosis in post-operative period if patient do not continue anti-platelet therapy.

It has been demonstrated in several studies that early initiation of anticoagulant therapy may diminish the risk of venous thrombosis (Segers A. J Thromb Haemost. 2008 August; 6(8):1313-8; Turpie et al., Lancet. 2009 May 1), however there is no consensus or standard antiplatelet therapy regimen designed to reduce the risk of arterial stent thrombosis in patients with implanted stents requiring surgical procedures.

Typically, at conclusion of surgical procedure a complete hemostasis is achieved, however, the risk of bleeding from the surgical site remains high during the first post-operative hours. Initiation of anti-platelet therapy during the immediate-early period after surgery may further increase that risk. Conversely, a delay of continuation of anti-platelet maintenance therapy will significantly increase the risk of stent thrombosis, considering that surgical procedure triggers platelet activation and aggregation. Therefore, an early therapy with reversible anti-platelet agent that could be titrated to a desirable level of platelet inhibition and have ultra-short platelet function recovery time could be beneficial in preventing stent thrombosis in that category of patients. Moreover, this type of agent will be safe because it may allow complete recovery of platelet function after discontinuation in case of bleeding.

Cangrelor is a potent, reversible and specific $P2Y_{12}$ receptor antagonist that would allow overcoming the limitations of currently used dual anti-platelet therapy with aspirin and clopidogrel thanks to its rapid onset and offset of action with steady-state plasma concentrations that can be achieved within minutes and titrated to modulate the level of platelet inhibition and most importantly, it is rapidly metabolized with an elimination half-life of <5 minutes, allowing complete recovery of platelet function in less than 60 min. Therefore, cangrelor could be an ideal anti-platelet agent for managing platelet inhibition in early post-operative period in patients with implanted stents requiring a surgical procedure.

The optimal platelet inhibitory dose and regimen for cangrelor infusion in post-operative period and transitioning to oral anti-platelet therapy can be determined.

The patient population can be ACS patients with implanted stents after PCI who require a major surgical procedure (CABG, GI anastomoses, pulmonary resection, prostatectomy, orthopedic procedures, etc.), N=40 subjects (4 groups with 10 subjects in each group). Cangrelor infusion will be initiated 1-2 hours after completion of surgical procedure at surgeons' discretion. The subjects will be randomized into the following groups:

Group 1: Cangrelor 0.5 µg/kg/min dose infusion for 24 hrs transitioning to oral antiplatelet therapy with 300 mg of clopidogrel loading dose after infusion discontinuation followed by 75 mg daily maintenance dose thereafter Group 2: Cangrelor 0.5 µg/kg/min infusion for 24 hrs transitioning to oral antiplatelet therapy with 600 mg of clopidogrel loading dose after infusion discontinuation followed by 75 mg daily maintenance dose thereafter Group 3: Cangrelor 1 µg/kg/min infusion for 24 hrs transitioning to oral antiplatelet therapy after infusion discontinuation transitioning to oral antiplatelet therapy with 300 mg of clopidogrel loading dose after infusion discontinuation followed by 75 mg daily maintenance dose thereafter Group 4: Cangrelor 1 µg/kg/min infusion for 24 hrs transitioning to oral antiplatelet therapy after infusion discontinuation transitioning to oral antiplatelet therapy with 600 mg of clopidogrel loading dose after infusion discontinuation followed by 75 mg daily maintenance dose thereafter The primary endpoints will be: (1) acute sent thrombosis during the 48 hrs after the surgical procedure, and (2) major and minor bleedings during the 48 hrs after the surgical procedure.

The methods of evaluation will be: (1) platelet aggregation using VerifyNow-P2Y12 test, (2) hemodynamic measurements, (3) blood tests, (4) clinical observations for minor capillary bleeding signs (petechia, hematoma), (5) Diagnostic imaging of intracranial, peritoneal and pleural cavities using CT, MRI, US, when necessary to detect potential bleeding complications (blood accumulation).

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

All documents, publications, patents, books, manuals, articles, papers, abstracts, posters and other materials referenced herein are expressly incorporated herein by reference in their entireties.

The invention claimed is:

1. A method of treating or inhibiting a disease or condition involving thrombosis in a subject in need of an invasive procedure who was previously treated with at least one thienopyridine, comprising administering to the subject prior to such invasive procedure an effective amount of cangrelor.

2. The method of claim 1, wherein the invasive procedure is a coronary artery bypass grafting.

3. The method of claim 1, wherein the invasive procedure is a percutaneous coronary intervention.

4. The method of claim 1, wherein the administration of cangrelor occurs within five days prior to the invasive procedure.

5. A method of treating or inhibiting a disease or condition involving thrombosis in a subject in need of an invasive procedure who was previously treated with at least one thienopyridine, comprising administering to the subject an effective amount of cangrelor to at least partially inhibit platelet activities of the subject.

6. The method of claim 5, wherein the subject has previously received a stent.

7. The method of claim 6, wherein the stent is a bare metal stent.

8. The method of claim 6, wherein the stent is a drug-eluting stent.

9. A method of at least partially inhibiting platelet activities in a subject in need thereof, comprising the steps of: administering an effective amount of at least one thienopyridine; and administering an effective amount of cangrelor after discontinuing the administration of the at least one thienopyridine.

10. The method of claim 9, wherein the at least one thienopyridine is non-reversible.

11. The method of claim 9, wherein the at least one thienopyridine is clopidogrel.

12. The method of claim 9, wherein the effective amount of cangrelor is an intravenous infusion of between 0.5 to 2.0 µg/kg/min.

13. The method of claim 9, wherein platelet inhibition is greater than approximately 60%.

14. The method of claim 9, wherein administration of cangrelor occurs within five days prior to an invasive procedure to be performed on the subject.

15. The method of claim 9, wherein administration of cangrelor occurs during an invasive procedure being performed on the subject.

16. The method of claim 9, wherein administration of cangrelor occurs after an invasive procedure performed on the subject.

17. A method of at least partially inhibiting platelet activities in a subject in need thereof previously treated with at least one thienopyridine, comprising administering to the subject an effective amount of cangrelor.

18. The method of claim 17, wherein the at least one thienopyridine is clopidogrel.

19. The method of claim 17, wherein administration of cangrelor begins at least five days prior to an invasive procedure.

20. The method of claim 19, wherein administration of cangrelor is discontinued between 1 and 24 hours prior to the invasive procedure.

21. A method of inhibiting a platelet activity in a subject in need thereof, comprising: (a) administering a therapeutically effective amount of at least one thienopyridine to the subject; (b) discontinuing administration of the at least one thienopyridine to the subject; and (c) administering a therapeutically effective amount of cangrelor to the subject, inhibiting platelet activity in the subject.

22. The method of claim 21, wherein the inhibitory activity of the at least one thienopyridine is non-reversible.

23. The method of claim 21, wherein the at least one thienopyridine is clopidogrel.

24. The method of claim 21, wherein the therapeutically effective amount of cangrelor is an intravenous infusion of between about 0.5 and about 2.0 µg/kg/min.

25. The method of claim 21, wherein the inhibition of platelet activity is an inhibition of greater than approximately 60% of platelet aggregation.

26. The method of claim 21, wherein the platelet activity is platelet aggregation.

27. The method of claim 21, wherein the discontinuation of administration of the at least one thienopyridine to the subject occurs at least five days prior to an invasive procedure to be performed on the subject.

28. The method of claim 27, wherein administration of cangrelor begins prior to the invasive procedure.

29. The method of claim 27, wherein administration of cangrelor begins during the invasive procedure.

30. The method of claim 27, wherein administration of cangrelor begins after the invasive procedure.

* * * * *